United States Patent
Fu et al.

(10) Patent No.: US 7,204,640 B2
(45) Date of Patent: Apr. 17, 2007

(54) APPARATUS AND METHOD FOR REGISTERING 2D RADIOGRAPHIC IMAGES WITH IMAGES RECONSTRUCTED FROM 3D SCAN DATA

(75) Inventors: Dongshan Fu, Santa Clara, CA (US); Gopinath Kuduvalli, San Jose, CA (US); Shehrzad Qureshi, Palo Alto, CA (US)

(73) Assignee: Accuray, Inc., Sunnyvale, CA (US)

( * ) Notice: Subject to any disclaimer, the term of this patent is extended or adjusted under 35 U.S.C. 154(b) by 0 days.

(21) Appl. No.: 10/652,786

(22) Filed: Aug. 29, 2003

(65) Prior Publication Data

US 2005/0047544 A1 Mar. 3, 2005

(51) Int. Cl.
*A61N 5/10* (2006.01)
(52) U.S. Cl. .................. 378/205; 378/65; 382/294
(58) Field of Classification Search .............. 378/4, 378/62, 63, 65, 205; 382/132, 128, 131, 382/294
See application file for complete search history.

(56) References Cited

U.S. PATENT DOCUMENTS

| | | | |
|---|---|---|---|
| 5,117,829 A * | 6/1992 | Miller et al. ............... | 600/427 |
| 5,901,199 A | 5/1999 | Murphy et al. | |
| 6,470,207 B1 | 10/2002 | Simon et al. | |
| 2004/0092815 A1* | 5/2004 | Schweikard et al. ........ | 600/425 |
| 2004/0267113 A1 | 12/2004 | Thomson | |

OTHER PUBLICATIONS

Penney et al., "A Comparison of Similarity Measures for Use in 2-D-3-D Medical Image Registration", IEEE Transactions on Medical Imaging, vol. 17, No. 4, Aug. 1998, pp. 586-595.*
Murphy, Martin J., "An automatic six-degree-of-freedom image registration algorithm for image-guided frameless stereotaxic radiosurgery", Medical Physics, Jun. 1997, vol. 24, Issue 6, pp. 857-866.*

(Continued)

*Primary Examiner*—Edward J. Glick
*Assistant Examiner*—Chih-Cheng Glen Kao
(74) *Attorney, Agent, or Firm*—Blakely, Sokoloff, Taylor & Zafman LLP

(57) ABSTRACT

A method and system is provided for registering a 2D radiographic image of a target with previously generated 3D scan data of the target. A reconstructed 2D image is generated from the 3D scan data. The radiographic 2D image is registered with the reconstructed 2D images to determine the values of in-plane transformation parameters (x, y, θ) and out-of-plane rotational parameters (r, Φ), where the parameters represent the difference in the position of the target in the radiographic image, as compared to the 2D reconstructed image. An initial estimate for the in-plane transformation parameters is made by a 3D multi-level matching process, using the sum-of-square differences similarity measure. Based on these estimated parameters, an initial 1-D search is performed for the out-of-plane rotation parameters (r, Φ), using a pattern intensity similarity measure. The in-plane parameters (x, y, θ) and out-of-plane parameters (r, Φ) are iteratively refined, until a desired accuracy is reached.

49 Claims, 5 Drawing Sheets

OTHER PUBLICATIONS

Graeme P. Penney, et al., "Validation of a two- to three-dimensional registration algorithm for aligning preoperative CT images and intraoperative fluoroscopy images," *Med. Phys.* 28(6), 1024-1032, Jun. 2001.

D. Sarrut, et al., "Patient positioning in radiotherapy by registration of 2D portal to 3D CT images by a contend-based research with similarity measures," *CARS 2000*, 707-712.

Martin J. Murphy, "An automatic six-degree-of-freedom image registration algorithm for image-guided frameless stereotaxic radiosurgery," *Med. Phys.* 24(6), 857-866, Jun. 1997.

International Search Report, International Application No. PCT/US04/27158, International filing date Aug. 20, 2004, mailed Sep. 6, 2005.

\* cited by examiner

APPARATUS AND METHOD FOR REGISTERING 2D RADIOGRAPHIC IMAGES WITH IMAGES RECONSTRUCTED FROM 3D SCAN DATA

FIELD OF THE INVENTION

The present invention relates to a method and system for registering 2D (two-dimensional) radiographic images with images reconstructed from 3D (three-dimensional) scan data. More particularly, the invention relates to a method and system for registering 2D stereo x-ray image data with digitally reconstructed radiographs of 3D CT scan data.

BACKGROUND

Medical image registration is useful in many areas of medicine, for example radiosurgery. In radiosurgery, tumors and other lesions are treated by delivering a prescribed high dose of high-energy radiation to the target area, while minimizing radiation exposure to the surrounding tissue. Radiosurgery therefore calls for an ability to accurately focus on a target region, so that only the target receives the desired high doses of radiation, while surrounding critical structures are avoided. Typically, 3D imaging modalities, such as computed tomography (CT), magnetic resonance (MR) imaging, or positron emission therapy (PET) are used to generate diagnostic 3D images of the anatomical region containing the targeted area, for treatment planning purposes. These tools enable practitioners to identify the anatomical organs of a patient, and to precisely locate any abnormalities such as tumors.

To correct patient position or align radiation beam, the change in target position at the time of treatment (as compared to the position at the time of the diagnostic treatment planning) needs to be detected. This is accomplished by registering the 2D image acquired at the treatment time with the 3D CT scan obtained at the time of treatment planning.

The target positions are defined using the 3D diagnostic CT scan by physicians at the time of treatment planning. CT scans allow an image of the internal structure of a target object to be generated, one cross-sectional slice at a time. The CT data is used as the reference to determine the patient position change during treatment. Typically, synthesized 2D images such as digitally reconstructed radiographs (DRRs) are generated from the 3D CT data, and are used as 2D reference images. Similarity measures are used to compare the image intensity in the x-ray and the DRR images, in order to determine the patient pose change. In the field of medical image registration, this problem is categorized as a 2D/3D registration.

The methods used in the 2D/3D registration procedure can be divided into two categories. The first category includes methods based on image features. The image features may be anatomical edges, or segmented objects. Registration accuracy depends on the accuracy of edge detection, or the accuracy of object segmentation. The main advantage of feature-based methods is computation speed. Because the full information content of the image is not used, however, accuracy is sacrificed. The second category includes methods based on image intensity content. In intensity-based methods, the original images are used for the registration process. Therefore, a good accuracy can usually be achieved. Because a lengthy computation time is required, however, intensity-based methods are not practical for purposes of radiosurgery, or for clinical practice in general.

Image-guided radiosurgery requires precise and fast positioning of the target at the treatment time. In practice, the accuracy should be below 1 mm, and the computation time should be on the order of a few seconds. Unfortunately, it is difficult to meet both requirements simultaneously, because of several reasons. First, the two different modality images, i.e. CT scan images and x-ray images, have different spatial resolution and image quality. Generally, x-ray image resolution and quality are superior to the resolution and quality of DRR images. Second, DRR generation relies on a proper attenuation model. Because attenuation is proportional to the mass density of the target volume through which the beam passes through, the exact relationship between the traversed mass density and the CT image intensity needs to be known, in order to obtain an accurate modeling. Establishing this relationship is difficult, so a linear attenuation model is often used. However, the skeletal structures in DRR images cannot be reconstructed very well using the linear model, the DRRs being only synthetic x-ray projection images. Finally, x-ray images usually have a large image size (512×512). For better registration accuracy, it is desirable to use the full resolution image. Full resolution images are rarely used, however, due to the extremely slow computation that results from using such images.

U.S. Pat. No. 5,901,199 by Murphy et al. (the "Murphy patent") describes a high-speed inter-modality image registration via iterative feature matching. The Murphy patent is a feature-based method. Prior to treatment, extraction and segmentation of silhouettes of the patient's skull are performed in order to make a feature mask. A set of DRR images are generated from the 3D CT data and are then masked, in order to isolate key pixels that are associated with anatomical edge features. The masked image contains only 5%–10% of the total image pixels. During treatment, the acquired x-ray images are similarly masked. The registration is conducted on the masked DRRs and the masked X-ray images. The registration process is completed in a few seconds. However, the accuracy and stability of the estimates are not sufficient to meet the sub-mm precision that is required in radiosurgery applications.

For these reasons, there is a need for a method and system for performing 2D/3D medical image registration using as little computing time as possible, while at the same time meeting the requisite accuracy for radiosurgical applications.

SUMMARY OF THE INVENTION

The present invention is directed to a precise and rapid method and system for registering 2D x-ray images with images that have been reconstructed from 3D scan data. A hierarchical and iterative framework for the registration algorithm permits a higher accuracy to be achieved, in both the translational and rotational adjustments. The total computation time is about an order of magnitude faster than other techniques existing in the prior art.

A method is provided for registering one or more 2D x-ray images of a treatment target with one or more 2D reconstructed images of the target that are based on previously generated 3D scan data. Preferably, the 2D reconstructed images are DRRs, generated using the same positions and angles of the imaging beams used for the x-ray images. The method includes performing in-plane rotations of the DRRs within the image plane of the x-ray images, thereby generating reference DRRs. The x-ray images are processed so that the orientation, image size, and bit depth of the x-ray images match the orientation, image size, and bit depth of the reference DRRs.

The method involves determining the value of parameters (x, y, θ) and (r, Φ) that are required for registering the x-ray image of the target with the reference DRRs of the target. (x, y, θ) represent the in-plane translational and rotational parameters within the image plane of the x-ray images, (x, y) indicating the requisite amount of translation within the image plane in the directions of the x- and y-axes, respectively, and θ indicating the requisite amount of rotation within the image plane. (r, Φ) represent the out-of-plane rotational parameters, and indicate the requisite amount of out-of-plane rotations about mutually orthogonal axes that are defined in a 3D coordinate system, and that are orthogonal to the image plane.

In order to determine these parameters, a 3D multi-level matching is first performed, in order to determine an initial estimate for the in-plane transformation parameters (x, y, θ). Based on these parameters (x, y, θ) obtained by 3D multi-level matching, an initial 1-D search is performed for each of the pair of out-of-plane rotation parameters (r, Φ). The in-plane translation parameters (x, y) are then refined, using 2D sub-pixel matching, to increase the accuracy of these parameters.

The in-plane rotation parameter (θ) is then refined, based on the out-of-plane rotation parameters (r, Φ) obtained from the initial 1D search, and on the updated in-plane transformation parameters (x,y), in order to increase the accuracy of the in-plane rotation parameter Φ. 1D interpolation is used in this step.

Next, each of the out-of-plane rotation parameters (r, Φ) are refined separately, based on the refined in-plane translation and rotation parameters. The refining steps are iteratively repeated, until a predetermined accuracy is reached. Finally, the out-of-plane rotation parameters (r, Φ) are refined, using 1D interpolation, in order to achieve the desired resolution.

DETAILED DESCRIPTION

Figure 1:
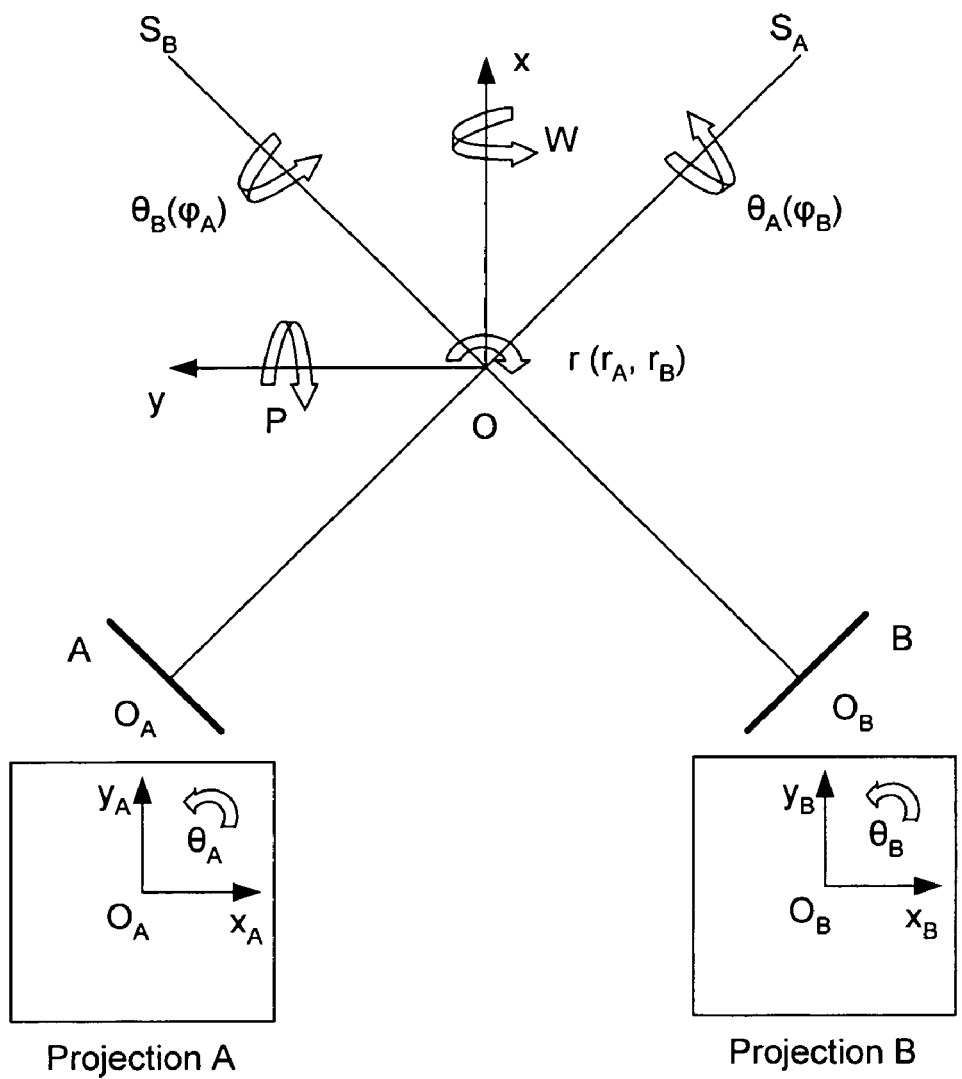
FIG. 1 illustrates the in-plane translational and rotational parameters (x,y,θ), and the out-of-plane rotational parameters (r, Φ), for registering a 2D radiographic image with previously generated 3D scan data.

The present invention is directed to an improved method and system for performing medical 2D/3D registration. The tracking method and system of the present invention is useful in radiosurgery and radiotherapy; however the method and system of the present invention can also be used in applications other than radiosurgery and radiotherapy, i.e. in any application where there a need to track rigid object by registering 2D radiographic images onto 3D scan data. While 2D x-ray images are described in the preferred embodiment of the present invention, the present invention can be used for the registration of any other type of 2D images onto 3D scan data.

In overview, the method of the present invention includes generating a reconstructed 2D image from the 3D scan data. The change in the position of the target (or other rigid object) in the radiographic image, as compared to the position of the target in the 3D scan data (as indicated in the reconstructed 2D image) is described using 3D rigid body transformations. The 2D x-ray image is registered onto the reconstructed 2D image, by determining the value of 3D rigid body transformation parameters that represent the difference in the position of the target as shown in the x-ray image as compared to the position of the target as shown by said 2D images reconstructed from said 3D scan data.

In radiosurgery, 2D/3D registration is necessary, for example, in order to correct patient position or properly align the radiosurgical beam. It is accomplished by registering the X-ray image acquired at the treatment time with the 3D CT scan obtained at the treatment planning time. In radiosurgery, the target positions are defined using a diagnostic 3D scan by physicians at the time of treatment planning. A CT scan is most frequently used, and will be described in the exemplary embodiments discussed in this section; however, it should be noted that other 3D scanning methods, such as MRI, ultrasound, or PET scanning, may also be used in other embodiments of the present invention. The 3D data is used as reference, to determine the patient position change during treatment. For this purpose, 2D reference images are reconstructed from the 3D scan data. Preferably, digitally reconstructed radiographs (DRR) are generated from 3D CT data, and are used as 2D reference images.

Because there are no external forces imposed on a treatment target during radiation treatment, it is reasonable to treat the treatment target as a rigid body, i.e. an object whose internal geometric relationships remain static or unchanged over time. The 3D rigid transformation can be described using the six degrees of freedom: three translations of the CT center and three rotations (roll, pitch and yaw) about three orthogonal axes. In the present invention, two orthogonal x-ray projections are utilized, in order to determine the six degrees of freedom, i.e. to solve for these six parameters (x, y, z, r, p, w). The registration in each projection is performed individually, and the results of the registration for each projection are subsequently combined, to obtain the six 3D transformation parameters.

The 2D x-ray projection images of the target are formed by transmitting imaging beams (having a known intensity, and having known positions and angles with respect to the target), generated from a respective pair of x-ray sources, through the target and onto cameras A and B. Each x-ray image A and B are characterized by a respective image plane, defined by mutually orthogonal x- and y-axes in a coordinate frame defined by the two x-ray cameras A and B: $x_A$ and $y_A$ for projection A, and $x_B$ and $y_B$ for projection B.

FIG. 1 illustrates the geometry of the in-plane translational and rotational parameters (x,y, θ), and the out-of-plane rotational parameters (r, Φ), in an embodiment of the invention in which a pair of orthogonal 2D projection images, A and B, are used. As illustrated in FIG. 1, a 3D CT coordinate system, i.e. a coordinate system for the target as viewed in the frame of the CT scan study (taken at the time of treatment planning), can be defined. During treatment, the patient assumes a position within the real-time camera coordinate frames (defined by the two x-ray cameras A and B, respectively), that does not necessarily match the position of the patient as seen from within the 3D CT coordinate system. The differences in the position and orientation of the anatomical target images within the respective radiographs (real-time x-ray, versus DRR) correspond to the difference in the three-dimensional position and orientation of the target between the camera- and the CT coordinate frames, and are found by solving for the parameters (x, y, z, r, p, w).

In the embodiment illustrated in FIG. 1, the x-axis in the 3D CT coordinate system is directed inward into the paper, and is not referenced. The 2D projections A and B are viewed from the directions $o_A s_A$ and $o_B s_B$ respectively. The directions of axis $x_A$ in the 2D projection in the camera A coordinates, and axis x in the 3D CT coordinates are opposite to each other. The direction of axis $x_B$ in the camera B coordinates, and axis x in the 3D CT coordinates, are the same.

As shown in FIG. 1, each projection is characterized by a respective set of transformation parameters, namely $(x_A, y_A, \theta_A, r_A, \Phi_A)$ for projection A, and $(x_B, y_B, \theta_B, r_B, \Phi_B)$ for projection B. The two out-of-plane rotations (with respect to the image plane) in projections A and B are denoted by $(r_A, \Phi_A)$ and $(r_B, \Phi_B)$ respectively, where r denotes the amount of rotation about the x-axis (in the 3D CT coordinate system), and $\Phi$ denotes the amount of rotation about the $o_A s_A$ axis (for projection B) or the $o_B s_B$ axis (for projection A). The in-plane translations and rotation in projections A and B are denoted $(x_A y_A \theta_A)$ and $(x_B y_B \theta_B)$, respectively. As easily seen from FIG. 1, $x_A y_A$ and $x_B y_B$ denote the amount of translations within the image planes for each projection (A and B) in the directions of the x- and y-axes that define each image plane ($x_{A-}$ and $y_{A-}$ for projection A, and $x_{B-}$ and $y_{B-}$ for projection B), while $\theta_A$ and $\theta_B$ denote the amount of rotation within each image plane about an axis (not shown) that is perpendicular to both the $x_{A-}$ (or $x_{B-}$) and $y_{A-}$ (or $y_{B-}$) axes.

As can be seen from FIG. 1, the out-of-plane rotation $\Phi_A$ in projection A is the same as the in-plane rotation $\theta_B$ in projection B, and the out-of-plane rotation $\Phi_B$ in projection B is the same as the in-plane rotation $\theta_A$ in projection A. The use of the two projections A and B thus over-constrains the problem of solving for the six degrees of freedom. It can be seen from FIG. 1 that $x_A = x_B$, $r_A = r_B$, $\theta_A = \Phi_B$ and $\theta_B = \Phi_A$.

For projection A, given a set of reference DDR images which correspond to different combinations of the two out-of-plane rotations $(r_A, \Phi_A)$, the 2D in-plane transformation $(X_A, Y_A, \Phi_A)$ can be estimated by the 2D image comparison. Determining the two out-of-plane rotations $(r_A, \Phi_A)$ relies on which reference DRR is used for best similarity match. Similarly, the 2D in-plane transformation $(X_B, Y_B, \theta_B)$ and the out-of-plane rotations $(r_B, \Phi_B)$ can be estimated for projection B.

In one embodiment of the present invention, digitally reconstructed radiographs (DRRs) are generated offline from the 3D CT scan, and used as references for determining the position of the patient and the target. In an exemplary embodiment, a set of reference DRRs is calculated that samples the full range of possible patient orientations. For example, the reference DRRs are calculated before treatment, by varying the orientation of the CT volumetric image of the target relative to the camera projection geometry. The reference DRRs are then stored for use in a lookup table during treatment. A comparison is made between the radiographs, acquired in real time, with each of the DRRs, to select the DRR that best matches the relevant real-time radiograph.

Figure 2:
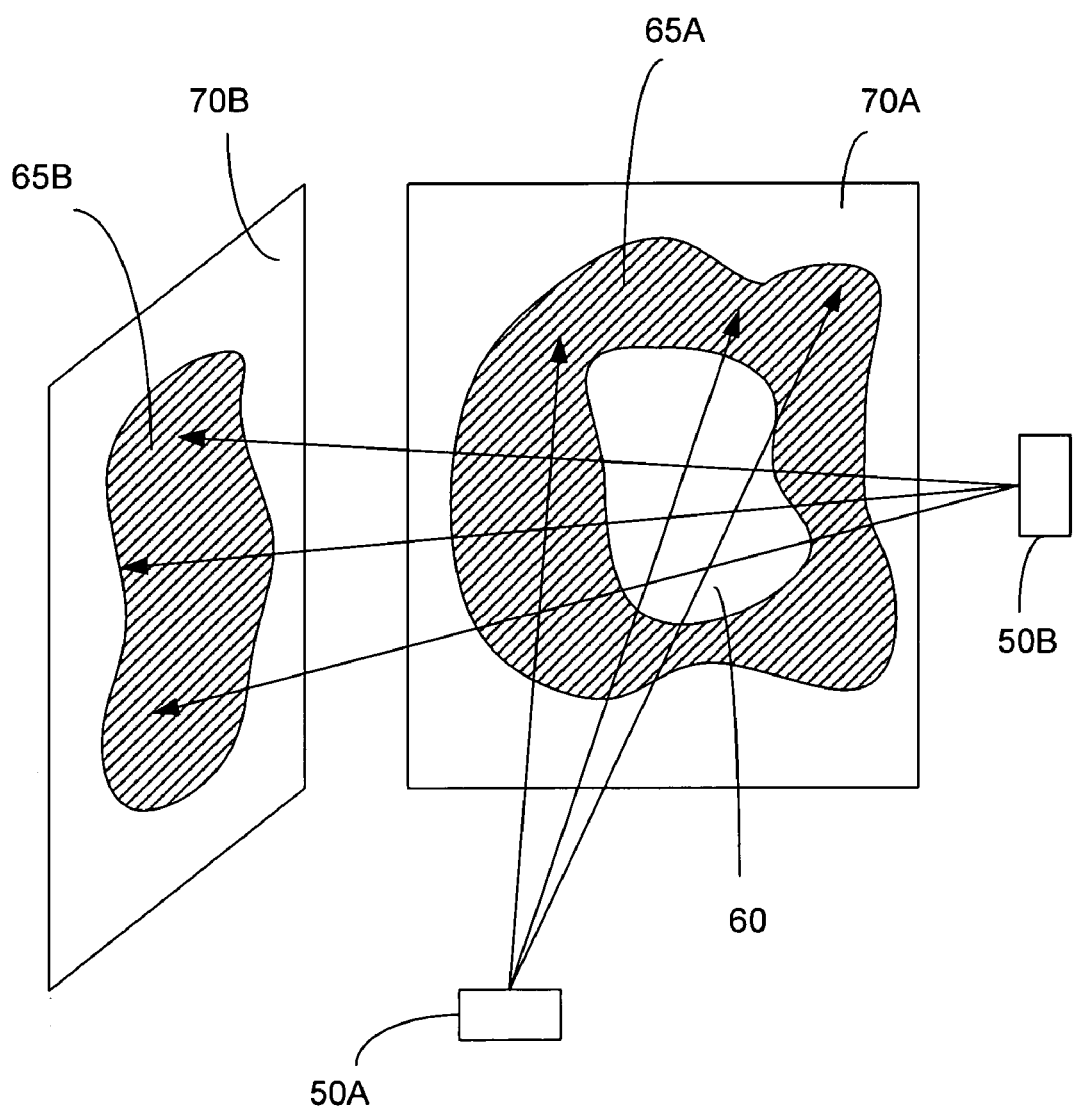
FIG. 2 illustrates the generation of 2D DRRs from 3D CT scan data of a treatment target within an anatomical region of a patient.

FIG. 2 illustrates the generation of a 2D DRR from 3D CT scan data of a treatment target within an anatomical region of a patient. In FIG. 2, the volumetric 3D CT image of the target is referred to with the aid of reference numeral 60. The DRRs 65A and 65B, shown in FIG. 2, are artificial, synthesized 2D images that represent the radiographic image of the target that would be obtained, if imaging beams were used having the same intensity, position and angle as the beams used to generate the real time x-ray projection images, and if the target were positioned in accordance with the 3D CT scan data. In other words, the DRRs are calculated from prior 3D CT data, in an exact emulation of the real-time camera perspectives. The reference numerals 50A and 50B illustrate the hypothetical positions and angles from which the imaging beams would be directed through a target positioned in accordance with the CT volumetric image 60 of the target.

Typically, DRRs are generated by casting hypothetical beams or rays through the CT volumetric image of the target. Each ray goes through a number of voxels of the 3D CT image 60. By integrating the CT numbers for these voxels along each ray, and projecting onto an imaging plane (shown as 70A and 70B, respectively, in FIG. 2), the resultant image would emulate the radiograph that would be obtained by passing rays from hypothetical camera locations and angles (shown schematically as 50A and 50B, respectively) through a target positioned in accordance with the volumetric 3D image 60. Ray tracing algorithms, known in the art, are generally used to generate the DRRs.

Figure 3:
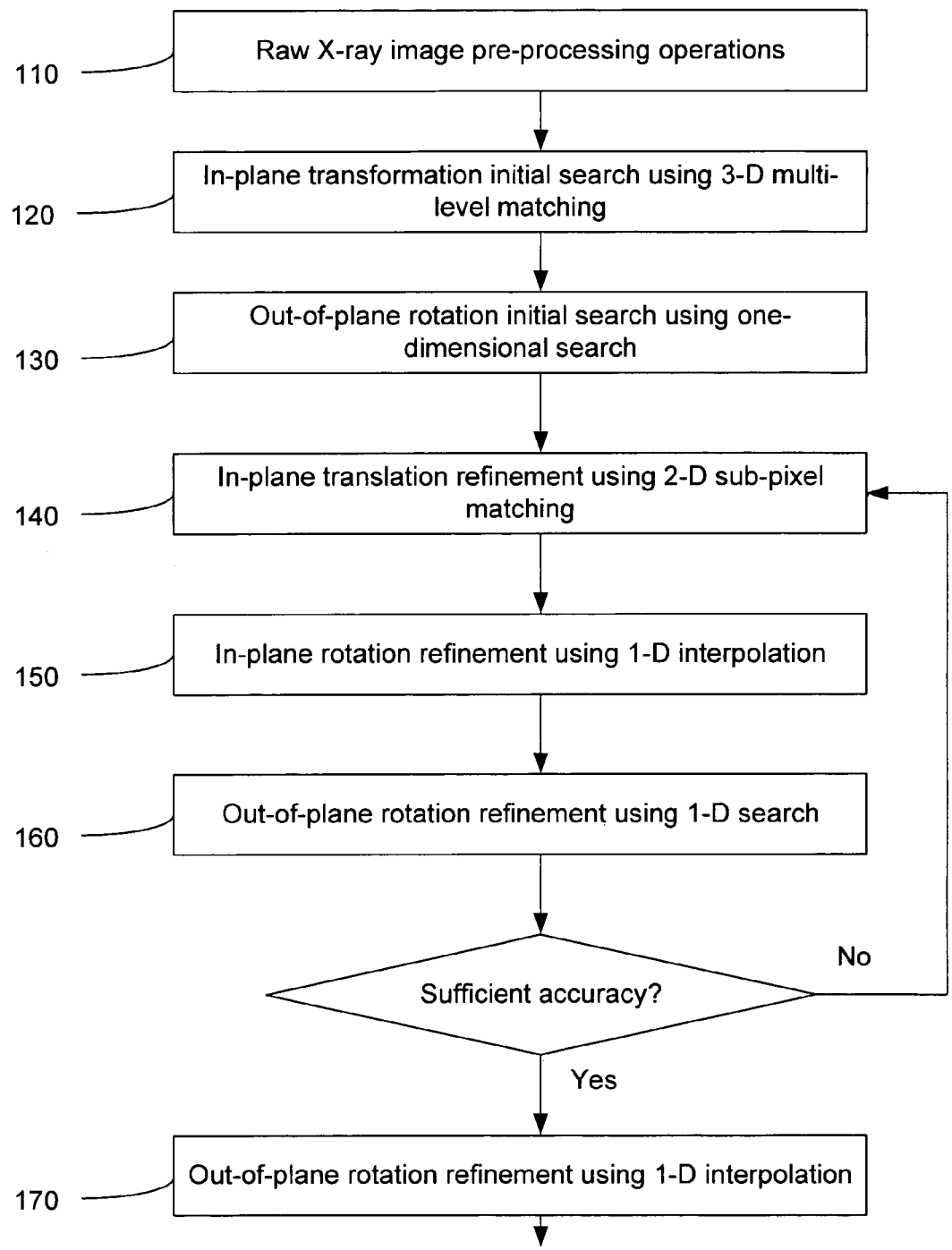
FIG. 3 illustrates a flowchart of the registration algorithm used in a 2D/3D registration method, in accordance with one embodiment of the present invention.

FIG. 3 illustrates a flowchart of the registration algorithm used in a 2D/3D registration method, performed in accordance with one embodiment of the present invention. In the present invention, the registration algorithm is designed in a hierarchical and iterative framework. The registration algorithm permits an accurate and rapid registration of a 2D x-ray image of a target with previously generated 3D scan data of the target.

As seen from FIG. 3, the first step (step 110 in FIG. 3) in the registration process is to pre-process the raw x-ray images, so that the orientation, image size, and bit depth of the x-ray image emulates the orientation, image size, and bit depth of the reconstructed 2D image.

In the embodiment of the present invention illustrated in FIG. 3, the registration process is described in terms of six distinct phases (illustrated in FIG. 3 as steps 120, 130, 140, 150, 160, and 170). In phase 1 (step 120 in FIG. 3), the in-plane transformation parameters (x, y, θ) are initially estimated using a set of in-plane rotated DRR images, which are generated offline from the nominal reference DRR (in 0 degree). The most intensive computation in the registration process is the computation of the in-plane rotation. To achieve a rapid computation, it is desirable to compute as many in-plane rotations as possible for the reference DRRs, before starting the registration process. The process of generating in-plane rotated DRRs is thus carried out offline, after the reference DRRs for out-of-plane rotations are generated. All the reference DRR images are stored in memory, and used for registering each real-time x-ray image that is acquired during patient alignment and treatment.

In step 120, the three parameters are rapidly searched using a 3D multi-level matching method (described in connection with FIG. 4 below). A sum of absolute differences method ("SAD"; described in co-pending, commonly owned U.S. patent application Ser. No. 10/652,717, (the "'717 application") entitled "Apparatus And Method For Determining Measure Of Similarity Between Images) is used as the similarity measure. In this step, there is no floating computation. The pixel accuracy for the translations (x,y) and half-degree accuracy for the in-plane rotation (θ) are achieved.

In the next step, i.e. step 130 (phase 2 of the registration process), the two out-of-plane rotations (r,Φ) are separately searched in one dimension, based on the values of the in-plane parameters (x, y, θ), determined in previous step 120. A plurality $N_r$ and $N_\Phi$ of out-of-plane rotation angles are determined, respectively, for said rotational parameters (r,Φ). A plurality $N_r*N_\Phi$ of 2D reference images are generated, one reference image for each of said plurality $N_r$ and $N_\Phi$ of said out-of-plane rotation angles. A more complicated similarity measure, based on pattern intensity (described in the '717 application), is used to detect the reference DRR image that corresponds to a combination of two out-of-plane rotations (r,Φ). The search space for the possible rotation angles is the full search range of out-of-plane rotation angles. For an initial estimate, the full search range is sampled at every one-degree interval. In step 140 (phase 3), the in-plane translation parameters (x, y) are refined using 2D sub-pixel matching. 2D sub-pixel matching is a full range search method. Based on the updated transformation parameters (x, y, θ, r, Φ) obtained from the previous step in the registration, a set of DRR images (3×3 or 5×5) is generated by translating the unknown reference DRR, one sub-pixel at a time. The in-plane translations (x, y) in sub-pixel accuracy are refined by finding the best match between the x-ray image and the DRR images.

In step 150 (phase 4), the in-plane rotation parameter θ is refined using 1 D interpolation, based on the updated values for the in-plane translation parameters (x, y) from step 140, and the updated values of the out-of-plane rotation parameters (x, Φ) from step 130. In step 160 (phase 5), the out-of-plane rotations are separately refined to a better accuracy using 1 D search, based on the updated values for the in-plane transformation parameters (x, y, θ), from steps 140 and 150. In steps 140, 150, and 160 (phases 3, 4, and 5), a similarity measure method based on pattern intensity (described in the '717 application) is used, to ensure higher accuracy.

Steps 140, 150, and 160 are iteratively repeated until, a sufficient accuracy is obtained. Once the desired accuracy is reached, the final out-of-plane rotations are 1D interpolated, in the final step 170 (6th and last phase) of the registration process.

Figure 4:
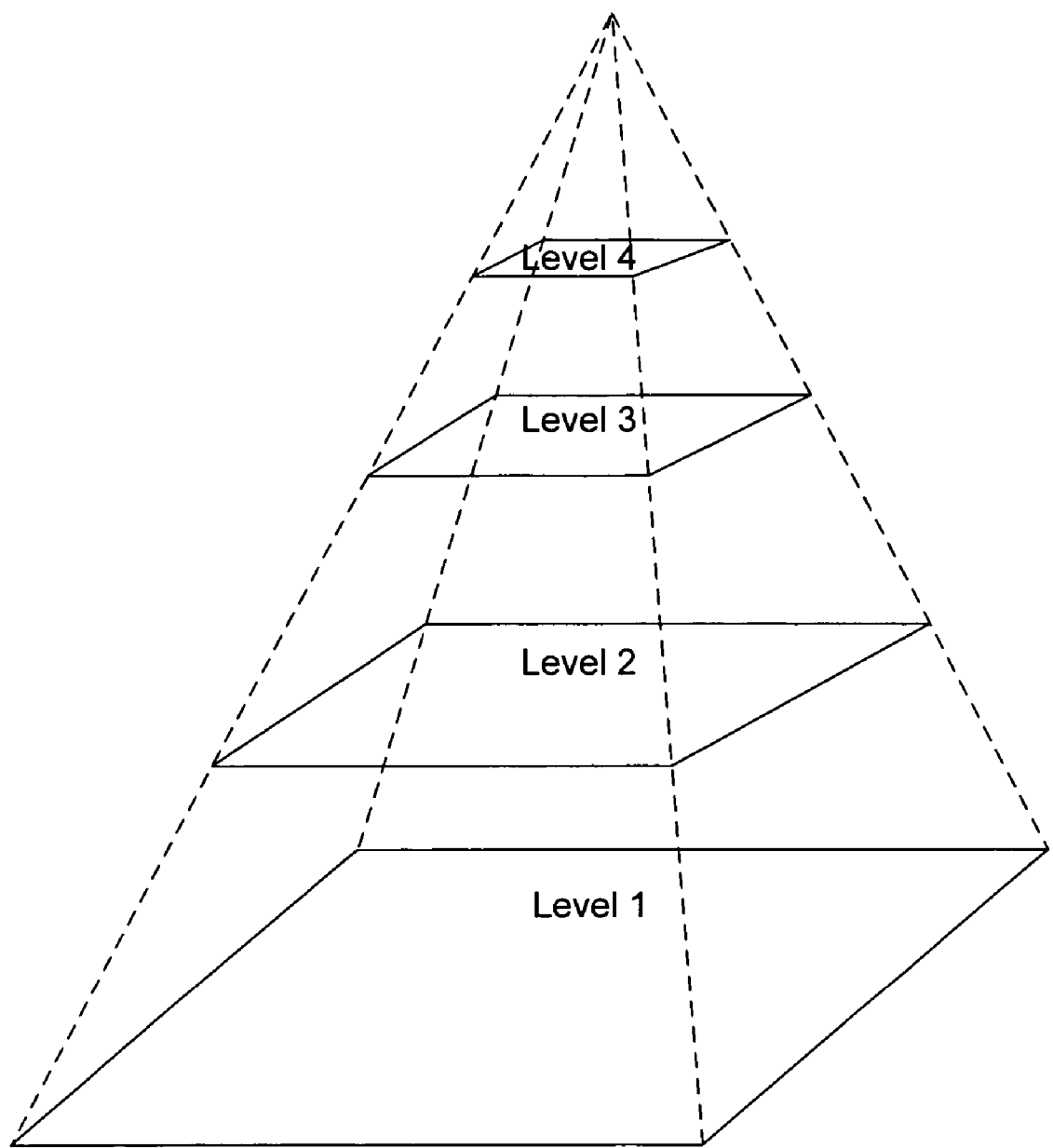
FIG. 4 illustrates a multi-resolution image representation for a multi-level matching process used to estimate the in-plane transformation parameters.

FIG. 4 illustrates a multi-resolution image representation for the multi-level matching process, used in the first phase (step 120 in FIG. 3) to initially estimate the in-plane transformation parameters. The full-size image is at the bottom (Level 1). The upper images (Level 2, Level 3 and Level 4) have lower spatial resolution. The lower resolution images are obtained by low pass filtering, and by sub-sampling of the full-size images.

As a fast search method, multi-level matching is used for an initial estimate the in-plane transformation parameters. The basic idea of multi-level matching is to match the images at each level successively, starting with the lowest image resolution level (Level 4). The results at the lower resolution level serve to provide rough estimates for the in-plane transformation parameters (x, y, θ). The output at a lower level is then passed to the subsequent level characterized by a higher resolution. The parameters (x, y, θ) are refined, using the higher resolution images. In the final results obtained through multi-level matching, the accuracy of the translations depends on the spatial resolution of the image having the highest resolution (Level 1). The accuracy of the rotations depends on the sampling intervals of the in-plane rotations, during the DRR initialization process described in paragraph 35 above.

There may be some risks inherent in multi-level matching. The estimates at lower levels may fall within local minima, and far away from global minima. In this case, further matching at subsequent levels (at higher resolutions) may not converge to the global minima. To overcome this risk, multiple candidates of estimates are used. Many candidates for an optimal matching at a lower level are passed on to the higher resolution level. The higher the number of candidates used, the more reliable are the estimates. The best candidates are ranked by the SAD values.

In FIG. 4, denoting the full image size in Level 1 by W×H, the image sizes are $$\frac{W}{2} \times \frac{H}{2}, \frac{W}{4} \times \frac{H}{4} \text{ and } \frac{W}{8} \times \frac{H}{8}$$

Level 2, Level 3 and Level 4, respectively. For translations, the search range in the lowest resolution level is the full search range that is calculated from the difference between the DRR and x-ray image sizes. Because of the smallest image size $$\frac{W}{8} \times \frac{H}{8}$$

at the lowest level, the full range search can be completed in a very short time. The same small search range is (−2, +2) pixels for the remaining resolution levels. Because of the small search range, the search can be completed quickly, even at large image sizes. For the rotations, the search range in the lowest resolution level is a full search range, at a denser sampling rate. In the higher resolution levels, partial search ranges are used, at a less dense sampling rate.

Figure 5:
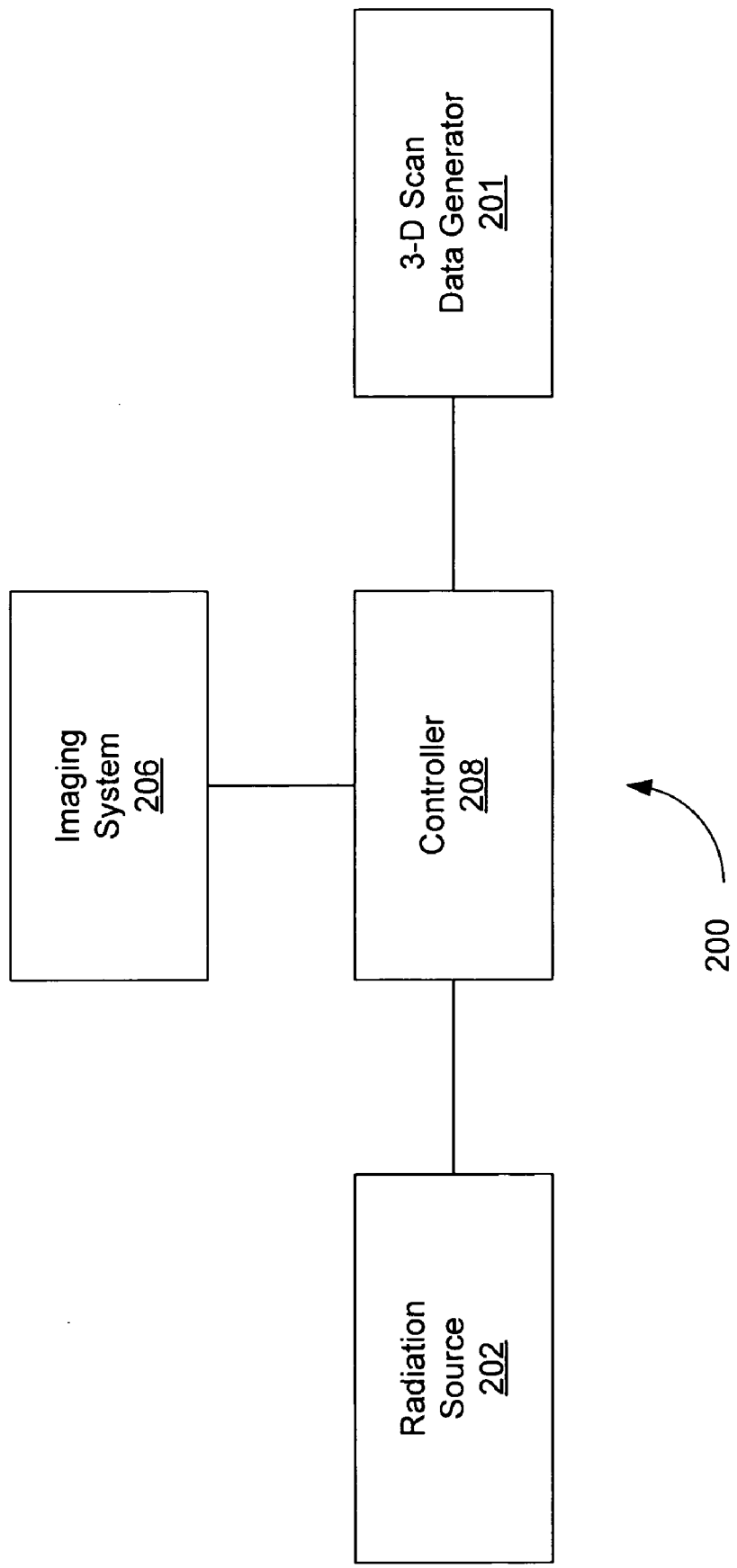
FIG. 5 illustrates a schematic block diagram of an apparatus for performing 2D/3D registration, in accordance with one embodiment of the present invention.

FIG. 5 illustrates a schematic block diagram of an apparatus 200 for performing 2D/3D registration, in accordance with one embodiment of the present invention. In overview, the apparatus 200 includes a means 201 for generating pre-treatment 3D scan data of the target; a radiation source 202; an imaging system 206; and a controller 208. The means 201 is a 3D scanner (for example a CT scanner, or an MRI scanner, or a PET scanner). The radiation source generates at least one radiographic imaging beam having a known intensity, and having a known position and angle relative to the target.

The controller 208 includes means for generating a set of 2D DRR images of the target, using the 3D scan data from the CT scanner, and using the known location, angle, and intensity of the imaging beam generated by the radiation source. The controller 208 also includes software for determining a set of in-plane transformation parameters (x, y, θ) and out-of-plane rotational parameters (r, Φ), the parameters representing the difference in the position of the target as shown in the x-ray image, as compared to the position of the target as shown by the 2D reconstructed images. The controller 208 includes means for determining the out-of-plane rotational parameters (r, Φ) configured to determine a plurality $N_r$ and $N_\Phi$ of out-of-plane rotation angles, respectively, for the rotational parameters (r, Φ). The means for generating a set of 2D DRR images of the target is configured to generate a plurality $N_r* N_\Phi$ of 2D reference images, one reference image for each of the plurality $N_r$ and $N_\Phi$ of the out-of-plane rotation angles.

The controller 208 further includes 1) software for performing a 3D multi-level matching to determine an estimate for the in-plane transformation parameters (x, y, θ); 2) software for performing a 1-D search for each of the pair of out-of-plane rotation parameters (r, Φ), based on the estimated in-plane parameters (x, y, θ); and 3) software for iteratively refining the in-plane parameters (x, y, θ) and the out-of-plane parameters (r, Φ), until a desired accuracy is reached.

In practice, a high accuracy is obtained for both translations and rotations after just a few iterations, using the method and system of the present invention. For translations, an accuracy of 0.5 mm or better is reached, and for rotations, an accuracy of 0.5 degrees or better is reached. The total computing time is a few seconds, which is an order of magnitude faster than other methods in the prior art.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of registering a 2D (two-dimensional) x-ray image of a target with previously generated 3D (three-dimensional) scan data of said target, said x-ray image being characterized by an image plane defined by mutually orthogonal x- and y-coordinates, the method comprising:
    A. generating at least one reconstructed image from said 3D scan data, said reconstructed image also characterized by the same image plane;
    B. determining the value of in-plane transformation parameters (x, y, θ) and out-of-plane rotational parameters (r, Φ) for registering said reconstructed image onto said x-ray image, said in-plane and out-of-plane parameters representing a difference in the position of the target as shown in said x-ray image as compared to the position of the target as shown by said image reconstructed from said 3D scan data;
        wherein r and Φ represent rotations of said target about first and second mutually orthogonal axes, said rotations being out-of-plane with respect to said image plane, said out-of-plane rotations representing a projection of said target onto said image plane;
        wherein x and y represent an amount of translation of said target within said image plane in the directions of said x- and y-axes, respectively, and θ represents an amount of rotation of said target within said image plane about an axis perpendicular to both said x- and said y-axes;
    and wherein step B comprises:
        a. obtaining an initial estimate for said in-plane transformation parameters (x, y, θ) by multi-level matching in 3D (three dimensions), between said x-ray image and said reconstructed image;
        b. based on said in-plane transformation parameters (x, y, θ) estimated in step a, performing an initial search in one dimension (1D) for each pair of out-of-plane rotation parameters (r, Φ); and
        c. iteratively refining said in-plane transformation parameters (x, y, θ) and said out-of-plane rotational parameters (r, Φ), until in-plane and out-of-plane parameters converge to a desired accuracy; and
    C. aligning a radiation source to the target using the values of the in-plane transformation parameters and the out-of-plane rotational parameters.

2. A method in accordance with claim 1, wherein said 3D multi-level matching is performed sequentially in each of a succession of a plurality of image resolution levels, starting at the lowest resolution level and ending at the highest resolution level.

3. A method in accordance with claim 1, further wherein said 2D x-ray image of said target is obtained by transmitting through said target an imaging beam having a known position and angle relative to said target, and wherein said reconstructed image is a 2D synthesized DRR (digitally reconstructed radiograph) representing a radiographic image of said target that would be obtained with said imaging beam at said known position and angle, if said target were positioned in accordance with said 3D scan data.

4. A method in accordance with claim 1, wherein determining the value of in-plane transformation parameters comprises:
    A. determining a plurality $N_r$ and $N_\Phi$ of out-of-plane rotation angles, respectively, for said rotational parameters (r, Φ); and
    B. generating a plurality $N_r*N_\Phi$ of 2D reference images, one reference image for each of said plurality $N_r$ and $N_\Phi$ of said out-of-plane rotation angles.

5. A method in accordance with claim 1, further comprising the step of generating offline, before step a, a plurality of in-plane rotated 2D reference images, by performing a series of in-plane rotations on said reconstructed image.

6. A method in accordance with claim 5, wherein said 3D matching process in step a is performed upon said in-plane rotated 2D reference images.

7. A method in accordance with claim 1, wherein said 3D matching process in step a is performed using a similarity measure method.

8. A method in accordance with claim 7, wherein said similarity measure method is based on a sum of absolute differences.

9. A method in accordance with claim 1, wherein step c of iteratively refining said in-plane and out-of-plane parameters comprises:
    d. refining the in-plane translation parameters (x, y), to increase the accuracy of said parameters;
    e. refining the in-plane rotation parameter (θ) based on said out-of-plane rotation parameters (r, Φ) searched in step b, and on said refined in-plane transformation parameters (x, y) from step d;
    f. separately refining each of the out-of-plane rotation parameters (r, Φ), based on said refined in-plane translation parameters from step d, and said refined rotation parameter from step e;
    g. iteratively and sequentially repeating steps d, e, and f, until a predetermined accuracy is reached; and
    h. refining once more said out-of-plane rotation parameters (r, Φ).

10. A method in accordance with claim 9, wherein step d of initially refining the in-plane translation parameters is performed by sub-pixel matching in two dimensions.

11. A method in accordance with claim 9, wherein step e of refining the in-plane rotation parameter is performed by 1D (one dimensional) interpolation.

12. A method in accordance with claim 9, wherein step f of separately refining said out-of-plane rotation parameters is performed through a 1D (one dimensional) search.

13. A method in accordance with claim 9, wherein step h of refining said out-of-plane rotation parameters (r, Φ) is performed by 1D interpolation.

14. A method in accordance with claim 9, wherein steps d, e, and f are performed using a similarity measure based on pattern intensity.

15. A method in accordance with claim 1, wherein said accuracy is sufficient to achieve a resolution of less than about 1 mm.

16. A method in accordance with claim 1, wherein said 3D scan data comprise at least one of CT scan data, MRI scan data, and PET (positron emission tomography) data.

17. A method in accordance with claim 1, wherein said 1D search for said out-of-plane rotation parameters in step b is performed using a similarity measure.

18. A method in accordance with claim 17, wherein said similarity measure is based on pattern intensity.

19. A method in accordance with claim 1, wherein search space for said 1D search in step b is the full search range of out-of-plane rotation angles, and said full search range is sampled by one degree increments.

20. A method in accordance with claim 1, further comprising the step of processing said 2D x-ray image, after step A and before step B, so as to match the orientation, image size, and bit depth of said x-ray image with the orientation, image size, and bit depth of said reconstructed image.

21. A system for registering at least one 2D radiographic image of a target with at least one image reconstructed from previously generated 3D scan data of said target, said radiographic image being characterized by an image plane defined by mutually orthogonal x- and y-axes, the system comprising:
  a. means for providing said 3D scan data of said target;
  b. a radiation source for generating at least one radiographic imaging beam having a known intensity, and having a known location and angle relative to said target;
  c. an imaging system for generating a 2D radiographic image of said target in near real time; and
  d. a controller, including:
    i) means for generating said at least one reconstructed 2D image of said target, using said 3D scan data, and using said known location, angle, and intensity of said imaging beam; and
    ii) software for determining a set of in-plane transformation parameters (x, y, θ) and out-of-plane rotational parameters (r, Φ), said in-plane and out-of-plane parameters representing a difference in the position of the target as shown in said radiographic image as compared to the position of the target as shown by said 2D reconstructed image;
  wherein said software comprises means fix performing a 3D multi-level matching to determine an initial estimate for said in-plane transformation parameters (x, y, θ);
  wherein r and Φ represent rotations of said target about first and second mutually orthogonal axes, said rotations being out-of-plane with respect to said image plane, said out-of-plane rotations representing a projection of said target onto said image plane; and
  wherein x and y represent an amount of translation of said target within said image plane in the directions of said x- and y-axes, respectively, and θ represents an amount of rotation of said target within said image plane about an axis perpendicular to both said x- and said y-axes.

22. A system in accordance with claim 21, wherein said software for determining said in-plane and out-of-plane rotational parameters comprises:
  means for performing a 1D search for each of the pair of out-of-plane rotation parameters (r, Φ) based on said initially estimated in-plane parameters (x, y, θ), and
  means for iteratively refining said in-plane parameters (x, y, θ) and said out-of-plane parameters (r, Φ), until a desired accuracy is reached.

23. A system in accordance with claim 22, wherein said 3D multi-level matching means performs sequentially in each of a succession of a plurality of resolution levels, starting at the lowest resolution level and ending at the highest resolution level.

24. A system in accordance with claim 22, wherein said 3D multi-level matching means comprises similarity measure means based on a sum of absolute differences.

25. A system in accordance with claim 22, wherein said means for iteratively refining said in-plane and out-of-plane parameters comprises:
  d. means for refining the in-plane translation parameters (x, y), to increase the accuracy of said parameters;
  e. means for refining the in-plane rotation parameter (θ) based on said out-of-plane rotation parameters (r, Φ) searched in step b, and on said refined h-plane transformation parameters (x, y) from step d;
  f. means for separately refining each of the out-of-plane rotation parameters (r, Φ), based on said refined in-plane translation parameters from step d, and said refined rotation parameter from step e; and
  g. means for iteratively and sequentially repeating steps d, e, and f, until a predetermined accuracy is reached, and for refining once more said out-of-plane rotation parameters (r, Φ).

26. A system in accordance with claim 22, wherein said means for refining the in-plane translation parameters comprises 2D sub-pixel matching means.

27. A system in accordance with claim 22, wherein said means for refining the in-plane rotation parameters comprises 1D (one dimensional) interpolation means.

28. A system in accordance with claim 22, wherein said means for separately refining said out-of-plane rotation parameters comprises means for performing one or more 1D searches.

29. A system in accordance with claim 22, wherein said means for refining said out-of-plane rotation parameters (r, Φ) comprises 1D interpolation means.

30. A system in accordance with claim 22, wherein said desired accuracy is sufficient to achieve a resolution of less than about 1 mm.

31. A system in accordance with claim 22, wherein means for performing a 1D search for said out-of-plane rotation parameters comprises means for performing a similarity measure based on pattern intensity.

32. A system in accordance with claim 22, wherein said means for refining the in-plane translation parameters (x, y), said means for refining the in-plane rotation parameter (θ), and said means for separately refining said out-of-plane rotation parameters (r, Φ) comprises means for performing one or more similarity measure.

33. A system in accordance with claim 22, further comprising means for processing said 2D x-ray image so as to match the orientation, image size, and bit depth of said x-ray image with the orientation, image size, and bit depth of said reconstructed image.

34. A system in accordance with claim 21, wherein said radiation source comprises an x-ray source, said 2D radiographic image comprises a 2D x-ray image, and said reconstructed image comprises a 2D DRR.

35. A system in accordance with claim 21, wherein said controller further comprises:
   A. means for determining a plurality $N_r$ and $N_\Phi$ of out-of-plane rotation angles, respectively, for said rotational parameters $(r, \Phi)$; and
   B. means for generating a plurality $N_r*N_{101}$ of 2D reference images, one reference image for each of said plurality $N_r$ and $N_\Phi$ of said out-of-plane rotation angles.

36. A system in accordance with claim 21, wherein said controller further comprises means for generating offline a plurality of in-plane rotated 2D reference images by performing a series of in-plane rotations on said reconstructed image.

37. A system in accordance with claim 21, wherein said 3D scan data comprise at least one of CT scan data, MRI scan data, and PET (positron emission tomography) data.

38. A method, comprising:
   acquiring x-ray images of a target volume in a first image plane and a second image plane, the x-ray images defining a present orientation of the target volume;
   generating synthetic x-ray reference images of the target volume from 3-dimensional scan data representing a previous orientation of the target volume, the synthetic x-ray reference images corresponding to in-plane transformations and out-of-plane rotations of the target volume projected onto the first image plane and the second image plane;
   determining a difference between the present orientation of the target volume and the previous orientation of the target volume in three translational coordinates and three rotational coordinates by comparing in-plane transformation parameters and out-of-plane rotation parameters of the x-ray images and the synthetic x-ray reference images in the first image plane and the second image plane, wherein determining said difference comprises searching the in-plane transformation parameters in the first image plane and the second image plane using a first similarity measure between the x-ray images and the synthetic x-ray reference images in a 3-dimensional multi-level search; and
   aligning a radiation source to the target volume using the difference between the present orientation of the target volume and the previous orientation of the target volume.

39. The method of claim 38, wherein the in-plane transformation parameters comprise two in-plane translation parameters and one in-plane rotation parameter in each of the first image plane and the second image plane, and wherein the out-of-plane rotation parameters comprise two mutually orthogonal rotations with respect to each of the first image plane and the second image plane.

40. The method of claim 39, further comprising processing the x-ray images to match image properties of the synthetic x-ray reference images, wherein determining the difference between the present orientation of the target volume and the previous orientation of the target volume further comprises:
   estimating the in-plane transformation parameters in the first image plane and the second image plane using a plurality of in-plane rotated synthetic x-ray reference images;
   searching the out-of-plane rotation parameters in the first image plane and the second image plane in a 1-dimensional search using a second similarity measure between the x-ray images and the synthetic x-ray reference images;
   refining the in-plane translation parameters in the first image plane and the second image plane using 2-dimensional sub-pixel matching between the x-ray images and the synthetic x-ray reference images;
   refining the in-plane rotation parameters in the first image plane and the second image plane using 1-dimensional interpolation based on the in-plane translation parameters and the out-of-plane rotation parameters; and
   refining the out-of-plane rotation parameters in the first image plane and the second image plane using a 1-dimensional search based on the refined in-plane translation and in-plane rotation parameters using the second similarity measure.

41. The method of claim 40, wherein the first similarity measure comprises a sum of absolute differences measure and the second similarity measure comprises an image pattern intensity measure.

42. The method of claim 40, wherein the 3-dimensional multi-level search comprises a four level search proceeding from a low resolution search at a first level, through progressively higher resolution searches at a second level and a third level, to a highest resolution search at a fourth level, a resolution parameter at each level defined by low pass filtering the x-ray images.

43. The method of claim 40, wherein processing the x-ray images to match image properties of the synthetic x-ray reference images comprises matching an orientation, an image size, and a bit depth of the x-ray images with an orientation, an image size, and a bit depth of the synthetic x-ray reference images.

44. A system, comprising:
   a radiation source and an imaging system to generate 2D radiographic images of a target volume in a first image plane and a second image plane, the 2D radiographic images defining a present orientation of the target volume;
   a 3D scan data generator to generate reconstructed 2D reference images of the target volume from 3D scan data representing a previous orientation of the target volume, the reconstructed 2D reference images corresponding to in-plane transformations and out-of-plane rotations of the target volume projected onto the first image plane and the second image plane; and
   a controller coupled with the radiation source, the imaging system and the 3D scan data generator, the controller configured to:
   determine a difference between the present orientation of the target volume and the previous orientation of the target volume in three translational coordinates and three rotational coordinates by comparing in-plane transformation parameters and out-of-plane rotation parameters of the 2D radiographic images and the reconstructed 2D reference images in the first image plane and the second image plane, wherein to determine said difference the controller is configured to search the in-plane transformation parameters in the first image plane and the second image plane using a first similarity measure between the 2D radiographic images and the reconstructed 2D reference images in a 3-dimensional multi-level search.

45. The system of claim 44, wherein the in-plane transformation parameters comprise two in-plane translation parameters and one in-plane rotation parameter in each of the first image plane and the second image plane, and wherein the out-of-plane rotation parameters comprise two mutually orthogonal rotations with respect to each of the first image plane and the second image plane.

46. The system of claim 45, the controller further to process the 2D radiographic images to match image properties of the reconstructed 2D reference images, wherein to determine the difference between the present orientation of the target volume and the previous orientation of the target volume, the controller is configured to:
estimate the in-plane transformation parameters in the first image plane and the second image plane using a plurality of in-plane rotated reconstructed 2D reference images; to
search the out-of-plane rotation parameters in the first image plane and the second image plane in a 1-dimensional search using a second similarity measure between the 2D radiographic images and the reconstructed 2D reference images; to
refine the in-plane translation parameters in the first image plane and the second image plane using 2-dimensional sub-pixel matching between the 2D radiographic images and the reconstructed 2D reference images; to
refine the in-plane rotation parameters in the first image plane and the second image plane using 1-dimensional interpolation based on the in-plane translation parameters and the out-of-plane rotation parameters; and to
refine the out-of-plane rotation parameters in the first image plane and the second image plane using a 1-dimensional search based on the refined in-plane translation and in-plane rotation parameters using the second similarity measure.

47. The system of claim 46, wherein yhe first similarity measure comprises a sum of absolute differences measure and the second similarity measure comprises an image pattern intensity measure.

48. The system of claim 46, wherein the 3-dimensional multi-level search comprises a four level search proceeding from a low resolution search at a first level, through progressively higher resolution searches at a second level and a third level, to a highest resolution search at a fourth level, a resolution parameter at each level defined by low pass filtering the 2D radiographic images.

49. The method of claim 46, the controller to process the 2D radiographic images to match an orientation, an image size, and a bit depth of the reconstructed 2D reference images.

* * * * *